(12) United States Patent
Neumann et al.

(10) Patent No.: US 6,229,028 B1
(45) Date of Patent: May 8, 2001

(54) PROCESS FOR THE EPOXIDATION OF ALKENES

(75) Inventors: Ronny Neumann, Kfar Saba; Mazal Dahan, Jerusalem, both of (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/424,787

(22) PCT Filed: May 27, 1998

(86) PCT No.: PCT/IL98/00245

§ 371 Date: Apr. 7, 2000

§ 102(e) Date: Apr. 7, 2000

(87) PCT Pub. No.: WO98/54165

PCT Pub. Date: Dec. 3, 1998

(30) Foreign Application Priority Data

May 29, 1997 (IL) .................................................. 120.942

(51) Int. Cl.[7] .................... C07D 301/06; C07D 301/08
(52) U.S. Cl. ............................................. 549/523; 549/533
(58) Field of Search ...................................... 549/523, 533

(56) References Cited

U.S. PATENT DOCUMENTS

| 4,864,041 | 9/1989 | Hill | 549/513 |
| 5,223,631 | 6/1993 | Cheng et al. | 549/535 |

FOREIGN PATENT DOCUMENTS

| 44 47 231 | 7/1996 | (DE) . |
| 195 19 008 | 11/1996 | (DE) . |
| 195 30 787 | 2/1997 | (DE) . |
| 0 043 192 | 1/1982 | (EP) . |

Primary Examiner—Ba K. Trinh
(74) Attorney, Agent, or Firm—Pillsbury Winthrop LLP

(57) ABSTRACT

The invention provides a process for the catalytic epoxidation of alkene comprising contacting a transition metal substituted polyoxometalate and molecular oxygen with alkene.

11 Claims, 1 Drawing Sheet

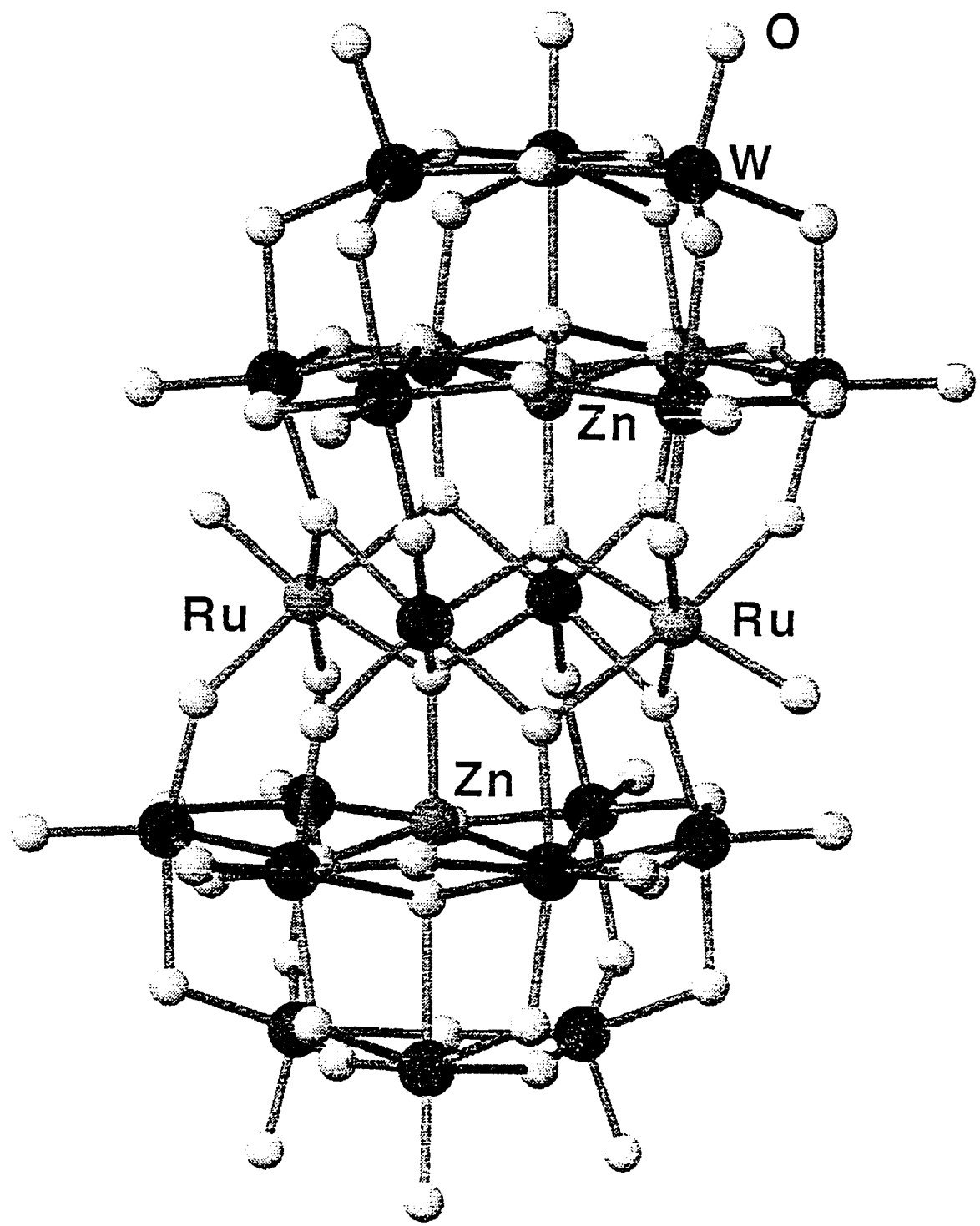

PROCESS FOR THE EPOXIDATION OF ALKENES

This application is a 371 of PCT/IL 98/00245 dated May 27, 1988.

TECHNICAL FIELD

The present invention relates to the catalytic activation of molecular oxygen for alkene epoxidation using transition metal substituted polyoxometalates as catalysts.

BACKGROUND ART

Epoxidation of alkenes is an important chemical transformation whereby an oxygen atom is added to a carbon-carbon double bond to form an epoxide. Epoxides are often utilized as intermediate compounds which can then be transformed to final products. Examples include but are certainly not limited to ethylene glycol and polyethylene glycol from ethylene oxide, propylene glycol from propylene oxide, phenylacetaldeyhyde from styrene oxide and propranolol from 2R-glycidol.

Epoxidation of alkenes can be carried out using numerous techniques. The oldest and probably most common method is to react the alkene with an organic peracid, according to the reaction set forth in equation (1).

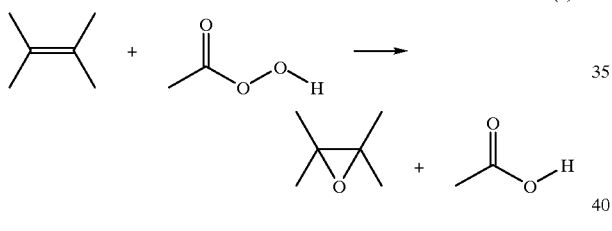

(1)

Typical peracids used in the art include perbenzoic acid, peracetic acid, performic acid, perphthalic acid and substituted perbenzoic acids such as 3-chloroperbenzoic acid. The salts of such acids may also be effective oxidants as in the case of magnesium monoperoxophthalate. The adds may be used as pure compounds or as prepared in situ in the reaction mixture by for example adding hydrogen peroxide to acetic anhydride to form peracetic acid. Although processes based on the reaction as described in equation (1) are known, there are certain drawbacks that are associated with such reactions. Among these one may site (a) the propensity for formation of by-products such as glycols and glycol esters by reaction of the epoxide with water and/or acid in the reaction medium, (b) the necessity of recovering and/or recycling the add co-product and (c) the necessity for stringent reaction control because of the safety danger involved in use of organic peracids (acyl hydroperoxides).

In order to minimize the danger in using peroxides as oxidants the use of alkyl and alkylaryl hydroperoxides in place of acyl hydroperoxides has been suggested and applied. These oxidants do not normally react with alkenes and the addition of a catalyst is required as shown in the reaction illustrated in equation (2).

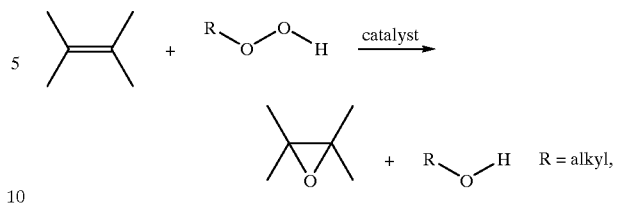

(2)

R = alkyl,

Some hydroperoxides commonly used in such reactions are tert-butylhydroperoxide, cumene hydroperoxide and ethylbenzene hydroperoxide. The catalysts used are most commonly based on compounds containing Ti(IV), V(V), Mo(VI) or W(VI) although many compounds based on other metals have been described as being effective catalysts. These reactions are safer because of the lower reactivity of alkyl and alkylaryl hydroperoxides compared to organic peracids, however, the other disadvantages associated with the use of acyl hydroperoxides remain. Thus, reactions are not necessarily more selective, since the presence of catalysts often leads to additional side reactions, for example, substitution and oxidation at the allylic carbon of the alkene instead of oxygen addition to the double bond. Similar to the problems encounter with the use of acyl hydroperoxides, the alcohol co-product must be recovered, recycled and/or otherwise utilized.

A further method to epoxidize alkenes is to use aqueous hydrogen peroxide as oxidant as shown in the reaction illustrated in equation (3).

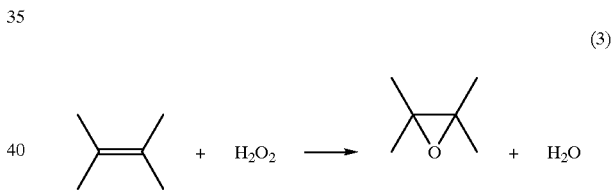

(3)

Such a reaction represents a conceptual improvement compared to the use of organic hydroperoxides in that the co-product is water and therefore is environmentally benign and need not be recovered or recycled. As in the use of alkyl- and alkylaryl hydroperoxides the presence of a catalyst is necessary, which catalysts are again often compounds containing Ti(IV), V(V), Mo(VI) or W(VI), among others. In only certain cases has high selectivity been reported for alkene epoxidation. Some effective and selective catalysts include titanium silicate-1 and other titanium substituted zeolites, and polyoxometalates such as $[WZnMn_2(ZnW_9O_{34})_2]^{12-}$ and $\{PO_4[WO(O_2)_2]_4\}^{3-}$. In many cases, the use of hydrogen peroxide represents an ideal oxidant provided reactions are selective. An exception is in cases where the low price of the epoxide make the use of hydrogen peroxide prohibitively expensive.

An additional important method for synthesis of epoxides from alkenes is via formation of a halohydrin, preferably a chlorohydrin, using hypochlorous acid in the first step, followed by use of base eg NaOH for ring closure in the second step, as shown in the reaction illustrated in equation (4).

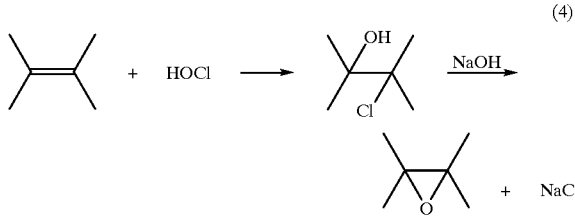

(4)

This is a very simple procedure which has, however, two problems. First, usually the presence of molecular chlorine in hypochlorous acid leads to formation of dichlorinated organics which are undesirable by-products and must be disposed of. Second, the process also forms large amounts of salts as co-product which also must be treated or recycled.

The ideal oxidant for alkene epoxidation both from an ecological and economic point of view would be molecular oxygen (dioxygen) as found in air. The addition of dioxygen to an alkene is disfavored kinetically, thus catalytic procedures need to be applied. In cases where there is no allylic carbon to the double bond, oxygen may be added to the double bond using a silver catalyst at elevated temperatures. In this way, ethylene oxide is manufactured from ethylene. For similar procedures with other alkenes, such as 1-butene, propene etc. this reaction fails to give epoxide in significant amounts. The basic problem in use of dioxygen for epoxidation of alkene lies in the radical nature of the molecular oxygen molecule. In homogenous reactions, this radical nature always leads to a preferred radical reaction via substitution of hydrogen at an allylic carbon atom. Therefore, the common mode of utilization of dioxygen in liquid phase catalyzed reactions does not yield epoxide as a major product The situation in gas phase reactions is similar wherein activation of alkenes leads to allylic type carbocations, carbanions or carbon radicals again preventing formation of epoxides as a significant product.

Conceptually, in order to use dioxygen for alkene epoxidation, activation of dioxygen should be via formation of a high valent metal oxo compound formed after scission of the oxygen-oxygen bond. These high valent metal-oxo intermediates are effective epoxidizing agents. Most commonly this is carried out in nature by use of monoxygenase type enzyme such as cytochrome P450 or methane monoxygenase. Such enzymes may be mimicked, for example, by using manganese and iron porphyrins as catalysts. The monooxygenase mechanism, however, requires two electrons from a reducing agent in order to cleave the oxygen-oxygen bond leading to formation of the high valent metal-oxo intermediate active in alkene epoxidation. From a process point of view the reducing agent becomes the limiting reagent instead of dioxygen and negates the attractivity of such a process.

The alternative is activation of dioxygen in a dioxygenase type mechanism. In such a reaction, dioxygen is cleaved using two metal centers leading to formation of two high valent metal-oxo species. This type of reaction has been only realized using a ruthenium substituted tetramesitylporphyrin (RuTMP). Turnover rates to epoxide are very low and the catalyst has limited stability.

The limited stability of porphyrin ligands has led to the suggestion that transition metal substituted polyoxometalates may be important alternative catalysts to metalloporphyrins as disclosed and discussed in Hill, U.S. Pat. No. 4,864,041. These catalysts would retain the high activity of their metalloporhyrin counterparts, however, are significantly more thermally and oxidatively stable, thus allowing their use as long living catalysts. This previous work describes the application of transition metal substituted polyoxometalates for the epoxidation of alkenes using oxygen donors such a iodosylbenzene. Other reported academic research has evolved from this report and has described alkene epoxidation using other oxygen donors such as tertfutyihydroperoxide, hydrogen peroxide and p-cyano-N, N-dimethylaniline-N-oxide. The use of transition metal substituted polyoxometalates as catalysts for alkene epoxidation with molecular oxygen: has never been described.

DISCLOSURE OF THE INVENTION

Accordingly, it is an object of this invention to provide a novel process for the epoxidation of alkenes using molecular oxygen as oxidant. It is also an object of this invention to provide a method for carrying out this epoxidation of alkenes with molecular oxygen using a transition metal catalyst. Furthermore, it is an objective of this invention to carry out said epoxidation using a transition metal substituted polyoxometalate as catalyst.

According to the present invention there has now been discovered a process which uses transition metal substituted polyoxometalates as catalysts for the epoxidation of alkenes with molecular oxygen.

More particularly the present invention provides a process for the catalytic epoxidation of alkene comprising contacting a transition metal substituted polyoxometalate and molecular oxygen with alkene.

The process described in this invention relates to the use of transition metal substituted polyoxometalates (TMSP) to catalyze the epoxidation of alkenes with molecular oxygen according to the following equation (5).

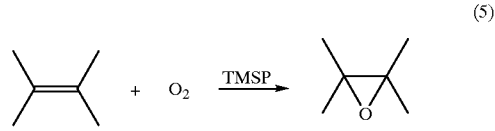

(5)

Polyoxometalates are oligomeric oxides of defined structure based on addenda of tungsten, molybdenum, niobium or vandium or a combination thereof. More specifically, transition metal substituted polyoxometalates are compounds of the general formula $X_x(TM)_yM_mO_z^{q-}$ where the heteroatom, X, if present (x__0) may be main group or transition metals, the addenda atoms, M, are molybdenum, tungsten, niobium or vanadium or a combination thereof, and TM is one or several different transition metals. The specific class of transition metal substituted polyoxometalates, $[WZnTM_2(XW_9O_{34})_2]^{q-}$, used in the process described by the present invention are characterized as a dimer of a truncated Keggin structure having a "belt" of W,Zn and other transition metal (TM) cations "sandwiched" between the two $B-XW_9O_{34}$ trivacant Keggin fragments the structure of which is shown in appended FIG. 1. The transition metal cations are assumed to be positioned at terminal positions and are hexacoordinate with at least one labile ligand such as water. The TM atom can be any transition metal of the first, second or third row. More preferably the TM atom is a noble metal selected from the group consisting of ruthenium, rhodium, palladium, osmium, iridium and platinum. Most preferably the TM atom is ruthenium. The heteroatom atom, X of the trivacant Keggin fragments can be any heteroatom known for Keggin compounds as is well-known in the art. For example, X can be a nonmetal such as phosphorous, silicon germanium, boron, or asenic. Alternatively X can be a metal such as zinc, cobalt, iron etc. The preferred transition metal substituted polyoxometalate for this process is $[WZnRu_2(ZnW_9O_{34})_2]^{11-}$. No transition metal substituted polyoxometalates or those of the general structure described and shown above have ever been used as catalysts for the epoxidation of alkenes with molecular oxygen. The counter cation of the above transition metal substituted polyoxometalates may be any cation including for example alkali metals, alkaline earth cations, transition metal cations or organic cations such as quaternary ammonium salts.

The catalytic reaction as described in equation (5) is carried out by contacting the catalyst with molecular oxygen and alkene. In one process the catalyst is contacted with molecular oxygen, followed by contact with the alkene. In another process the catalyst is contacted simultaneously with both the molecular oxygen and alkene. The reaction or contact between the catalyst and reactants (alkene and molecular oxygen) may take place in a solvent whereby the reactants are added to the catalyst dissolved in an liquid phase. Some typical solvents are aliphatic, aromatic or halogenated hydrocarbons. Some exemplary solvents of these classes are 1,2-dichloroethane, heptane, toluene, xylene, chlorobenzene or mixtures thereof. Alternatively, the catalyst may be placed on a support or used as a simple solid followed by addition of the reactants. The support used for the catalyst may be any support used in heterogenous catalysis including among others silica, alumina and other oxides.

The alkenes applicable as reactants in this process may be any type of alkenes known. This includes simple terminal and linear alkenes such as ethene, propene, 1-butene, 1-octene etc. The alkene may be an internal branched or linear alkene such as 2-butene, 2-octene, 2-methyl-2heptene, 2,3dimethyl-2butene, etc. The alkene may also be cyclic for example cyclohexene, cyclooctene, norbomene, etc. Molecular oxygen may be used pure, as air, as oxygen enriched air, or as oxygen depleted air. Inert gases may be added. The suggested temperature range of the reaction is between 0 and 350° C. More preferably between 25 and 250° C. and most preferably between 60 and 180° C. The reaction may be operated at atmospheric, sub-atmospheric or super-atmospheric pressures. Most preferably the reaction is run at super-atmospheric pressures.

While the invention will now be described in connection with certain preferred embodiments in the following examples and with reference to the accompanying figures so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

BRIEF DESCRIPTION OF THE DRAWINGS

FIG. 1 illustrates the molecular structure of an exemplary transition metal substituted polyoxometalate, $[WZnRu_2(ZnW_9O_{34})_2]^{11-}$, active in the catalysis of molecular oxygen addition to alkenes to form epoxides.

EXAMPLE 1

A 5 ml solution of degassed 1,2-dichloroethane containing 100 μmol $Q_{11}WZnRu_2(ZnW_9O_{34})_2$ in which Q is tricaprylmethyl ammonium was kept under 1 atm molecular oxygen at 90° C. for nine hours in a closed vessel. The oxygen solution was cooled to room temperature and 11.2 mg cyclooctene was added. After 2 hours the solution was analyzed by GLC. The analysis showed a 67.5% conversion to cyclooctene oxide.

EXAMPLE 2

A 5 ml solution of degassed 1,2-dichloroethane containing 100 μmol $Q_{11}WZnRu_2(ZnW_9O_{34})_2$ in which Q is tricaprylmethyl ammonium was kept under 1 atm molecular oxygen at 120° C. for six hours in a closed vessel. The oxygen solution was cooled to room temperature and 11.2 mg cyclooctene was added. After 2 hours the solution was analyzed by GLC. The analysis showed a 72.1% conversion to cyclooctene oxide.

EXAMPLE 3

A 5 ml solution of degassed 1,2-dichloroethane containing 100 μmol $Q_{11}WZnRu_2(ZnW_9O_{34})_2$ in which Q is tricaprylmethyl ammonium was kept under 1 atm molecular oxygen at 90° C. for nine hours in a closed vessel. The oxygen solution was cooled to room temperature and 9.4 mg norbomene was added. After 2 hours the solution was analyzed by GLC. The analysis showed a 82.1% conversion to norbomene oxide.

EXAMPLE 4

A 5 ml solution of degassed toluene containing 100 μmol $Q_{11}WZnRu_2(ZnW_9O_{34})_2$ in which Q is tricaprylmethyl ammonium was kept under 1 atm molecular oxygen at 90° C. for nine hours in a closed vessel. The oxygen solution was cooled to room temperature and 11.2 mg cyclooctene was added. After 2 hours the solution was analyzed by GLC. The analysis showed a 63.7% conversion to cyclooctene oxide.

EXAMPLE 5

A 5 ml solution of degassed 1,2-dichloroethane containing 100 μmol $Q_{11}WZnRu_2(ZnW_9O_{34})_2$ in which Q is tricaprylmethyl ammonium was kept under 1 atm molecular oxygen at 90° C. for nine hours in a closed vessel. The oxygen solution was cooled to room temperature and 8.4 mg 2,3dimethyl-2butene was added. After 2 hours the solution was analyzed by GLC. The analysis showed a 78.4% conversion to 2,3-dimethyl-2butene oxide.

EXAMPLE 6

A 5 ml solution of degassed 1,2-dichloroethane containing 100 μmol $Q_{11}WZnRu_2(ZnW_9O_{34})_2$ in which Q is tticaprylmethyl ammonium was kept under 1 atm molecular oxygen at 90° C. for nine hours in a closed vessel. The oxygen solution was cooled to room temperature and the solution was purged and repressurized with 1 atm propene. After 2 hours at 80° C. the solution was analyzed by GLC. The analysis showed 96% propene oxide and 4% acrolein as the only products.

EXAMPLE 7

A 5 ml solution of degassed 1,2-dichloroethane containing 100 μmol $Q_{11}WZnRu_2(ZnW_9O_{34})_2$ in which Q is tricaprylmethyl ammonium was kept under 1 atm molecular oxygen at 120° C. for six hours in a closed vessel. The oxygen solution was cooled to room temperature and the solution was purged and repressurized with 1 atm propene. After 2 hours at room temperature the solution was analyzed by GLC. The analysis showed 98% propene oxide and 2% acrolein as the only products.

EXAMPLE 8

A 5 ml solution of degassed 1,2-dichloroethane containing 100 μmol $Q_{11}WZnRu_2(ZnW_9O_{34})_2$ in which Q is tricapryimethyl ammonium was kept under 1 atm molecular oxygen at 90° C. for 18 hours in a closed vessel. The oxygen solution was cooled to room temperature and 11.2 mg 1 octene was added. After 18 hours at 60° C. the solution was analyzed by GLC. The analysis showed a 76% conversion to 1 octene oxide.

EXAMPLE 9

A 5 ml solution of degassed toluene containing 2.5 μmol $Q_{11}WZnRu_2(ZnW_9O_{34})_2$ in which Q is tricaprylmethyl ammonium and 280 mg was kept under 5 atm molecular oxygen at 90° C. for 24 hours in a closed vessel. After cooling GLC analysis showed a 15% conversion of cyclooctene to cyclooctene oxide.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the catalytic epoxidation of an alkene comprising contacting said alkene with molecular oxygen and with a transition metal substituted polyoxometalate of the formula $Q[Ru_2\ Zn\ W\ (X\ W_9\ O_{34})_2]^{q-}$, wherein X is a heteroatom selected from Zn, Co, Fe, P, Si, Ge, B and As, q is the charge of $[Ru_2\ Zn\ W\ (X\ W_9O_{34})_2]$ and Q is a counter cation.

2. A process according to claim 1 wherein X is selected from Zn and Co.

3. A process according to claim 1 wherein said counter cation is a cation selected from an alkali, alkaline earth or transition metal cation or an organic cation.

4. A process according to claim 1 wherein said transition metal substituted polyoxometalate has the formula $[Ru_2Zn\ W\ (X\ W_9\ O_{34})_2]^{11-}Q_{11}$.

5. A process according to claim 4 wherein Q is tricaprylmethyl ammonium and X is Zn.

6. A process according to claim 1 wherein said alkene is selected from the group consisting of branched, linear and cyclic alkenes.

7. A process according to claim 1 wherein said transition metal substituted polyoxometalate is first contacted with molecular oxygen, followed by contact with said alkene.

8. A process according to claim 1 wherein said transition metal substituted polyoxometalate is simultaneously contacted with molecular oxygen and with said alkene.

9. A process according to claim 1 wherein said epoxidation is carried out at a temperature in the range of between 25° C. and 250° C.

10. A process according to claim 1 wherein said epoxidation is carried out at super-atmospheric pressure.

11. A process according to claim 1 wherein said molecular oxygen is diluted with at least inert gas.

* * * * *